United States Patent
Miyahara et al.

(10) Patent No.: US 10,321,815 B2
(45) Date of Patent: Jun. 18, 2019

(54) IMAGE PICKUP MODULE AND ENDOSCOPE

(71) Applicant: OLYMPUS CORPORATION, Tokyo (JP)

(72) Inventors: Hideharu Miyahara, Tastuno-machi (JP); Youhei Sakai, Ina (JP); Yusuke Nakagawa, Tastuno-machi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/004,516

(22) Filed: Jun. 11, 2018

(65) Prior Publication Data
US 2018/0353060 A1 Dec. 13, 2018

Related U.S. Application Data

(63) Continuation of application No. PCT/JP2015/086192, filed on Dec. 25, 2015.

(51) Int. Cl.
*G02B 6/04* (2006.01)
*A61B 1/05* (2006.01)
(Continued)

(52) U.S. Cl.
CPC .......... *A61B 1/051* (2013.01); *A61B 1/00013* (2013.01); *A61B 1/00117* (2013.01);
(Continued)

(58) Field of Classification Search
CPC ... G02B 6/08; G02B 6/06; G02B 6/04; G02B 6/4249; Y10S 385/901
See application file for complete search history.

(56) References Cited

U.S. PATENT DOCUMENTS 7,133,138 B2 * 11/2006 Horii ............... G01B 9/0201
356/497
9,243,761 B2 * 1/2016 Nakanishi .......... G03B 21/2033
(Continued)

FOREIGN PATENT DOCUMENTS

JP  2004-170668 A  6/2004
JP  2013-025092 A  2/2013
(Continued)

OTHER PUBLICATIONS

International Search Report dated Feb. 9, 2016 issued in PCT/JP2015/086192.

*Primary Examiner* — Jennifer Doan
(74) *Attorney, Agent, or Firm* — Scully, Scott, Murphy & Presser, P.C.

(57) ABSTRACT

An image pickup module includes: an optical waveguide plate that includes a first waveguide, a second waveguide, and a third waveguide optically coupled to the first waveguide and the second waveguide through a branch portion; an image pickup device; a first optical device and a second optical device both mounted on the optical waveguide plate; an optical fiber; a ferrule into which the optical fiber is inserted; and a plurality of conductive wires. The ferrule includes a notch on a front surface, and distal end portions of the conductive wires are held between the optical waveguide plate and a surface of the notch of the ferrule. The other components are disposed within a plane of projection of the image pickup device.

8 Claims, 6 Drawing Sheets

(51) Int. Cl.
*H01L 27/14* (2006.01)
*H04N 5/369* (2011.01)
*A61B 1/00* (2006.01)
*A61B 1/07* (2006.01)

(52) U.S. Cl.
CPC ............ *A61B 1/00126* (2013.01); *A61B 1/07* (2013.01); *H01L 27/14* (2013.01); *H04N 5/369* (2013.01); *A61B 1/00165* (2013.01)

(56) References Cited

U.S. PATENT DOCUMENTS

| | | |
|---|---|---|
| 2013/0242310 A1 | 9/2013 | Matsuu |
| 2014/0055583 A1 | 2/2014 | Kato |
| 2014/0097459 A1 | 4/2014 | Motohara |
| 2017/0315310 A1* | 11/2017 | Nakagawa ............... G02B 6/42 |

FOREIGN PATENT DOCUMENTS

| | | |
|---|---|---|
| JP | 2013-188466 A | 9/2013 |
| JP | 2013-197237 A | 9/2013 |
| JP | 2014-102395 A | 6/2014 |

* cited by examiner

IMAGE PICKUP MODULE AND ENDOSCOPE

CROSS REFERENCE TO RELATED APPLICATION

This application is a continuation application of PCT/JP2015/086192 filed on Dec. 25, 2015, the entire contents of which are incorporated herein by this reference.

BACKGROUND OF INVENTION

1. Field of the Invention

The present invention relates to an image pickup module that includes an optical waveguide plate, an image pickup device, a first optical device, a second optical device, one optical fiber, a ferrule, and a plurality of conductive wires, and to an endoscope that includes the image pickup module at a distal end portion of an insertion section.

2. Description of the Related Art

An electronic endoscope includes an image pickup device such as a CCD, at a distal end portion of an elongated insertion section. In recent years, use of an image pickup device including a large number of pixels to the endoscope has been progressing. In a case where the image pickup device including the large number of pixels is used, an amount of image pickup signals to be transmitted from the image pickup device to a signal processing apparatus (processor) is increased. Therefore, optical signal transmission through a thin optical fiber is preferable as an alternative to electric signal transmission through a metal wiring.

In optical signal transmission, a light emitting device (E/O conversion device) that converts an electric signal into an optical signal, and a light receiving device (O/E conversion device) that converts the optical signal into the electric signal are used.

For example, Japanese Patent Application Laid-Open Publication No. 2013-025092 discloses an image pickup module that includes an optical device, a substrate, and a holding portion. The optical device performs input or output of an optical signal, and is mounted on the substrate. The holding portion includes a through hole into which an optical fiber that transmits the optical signal inputted or outputted from/to the optical device is inserted and is adjacently disposed in a thickness direction of the optical device.

Using bidirectional optical communication technology allows for transmission of the image pickup signal from the image pickup device to the signal processing apparatus and transmission of a control signal from the signal processing apparatus to the image pickup device through one optical fiber. In the bidirectional optical communication, for example, a first optical signal generated by the light emitting device and a second optical signal received by the light receiving device are multiplexed/demultiplexed.

In an endoscope using an image pickup device including ultrahigh resolution in which an information amount of the image pickup signal is even larger, it is difficult to transmit the optical image pickup signal through one optical fiber. However, when the image pickup signal is divided, respective divided image pickup signals are converted into optical image pickup signals with different wavelengths by the light emitting device, and the two optical image pickup signals are multiplexed, it is possible to transmit the image pickup signal through one optical fiber.

The optical signal is multiplexed/demultiplexed by an optical waveguide plate. For example, Japanese Patent Application Laid-Open Publication No. 2004-170668 discloses a polymer optical waveguide plate on which a Y-shaped branch portion is formed. The light emitting device is disposed at an end part of a first optical waveguide branch, and the light receiving device is disposed at an end part of a second optical waveguide branch. The first optical waveguide branch and the second optical waveguide branch are optically coupled to an optical waveguide main body at the Y-shaped branch portion.

To mitigate invasiveness of the endoscope, reduction in diameter and size of a rigid distal end portion is important. Therefore, it is desirable to reduce a diameter and a size of an image pickup module that is arranged at the distal end portion and includes the optical waveguide plate multiplexing/demultiplexing the optical signal.

SUMMARY OF THE INVENTION

An image pickup module according to an embodiment of the present invention includes: a polymer optical waveguide plate that includes a first main surface and a second main surface, and includes a first waveguide, a second waveguide, and a third waveguide, the second main surface being opposite to the first main surface, the third waveguide being optically coupled to the first waveguide and the second waveguide through a branch portion, and the first waveguide, the second waveguide, and the third waveguide being formed in parallel to the first main surface and the second main surface; an image pickup device including a light receiving surface and a rear surface, the rear surface being opposite to the light receiving surface and being disposed opposite to the first main surface of the optical waveguide plate; a first optical device and a second optical device mounted on the optical waveguide plate; one optical fiber disposed perpendicularly to the second main surface of the optical waveguide plate; a ferrule that includes a front surface and a rear surface, and includes a through hole into which the optical fiber is inserted and fixed, the rear surface being opposite to the front surface, the front surface being disposed opposite to the second main surface of the optical waveguide plate, and the through hole penetrating through the front surface to the rear surface; and a plurality of conductive wires respectively electrically connected to any one of the image pickup device, the first optical device, and the second optical device. The optical waveguide plate includes a reflection surface at an end part of the third waveguide, the first waveguide is optically coupled to the first optical device, the second waveguide is optically coupled to the second optical device, the third waveguide is optically coupled to the optical fiber through the reflection surface, the ferrule includes a notch on the front surface, distal end portions of the plurality of conductive wires are held between the second main surface of the optical waveguide plate and a surface of the notch of the ferrule, and the optical waveguide plate, the first optical device, the second optical device, the optical fiber, the ferrule, and the plurality of conductive wires are disposed within a plane of projection of the image pickup device as observed from an optical axis direction.

In addition, an endoscope according to another embodiment includes an image pickup module at a rigid distal end portion of an insertion section. The image pickup module includes: a polymer optical waveguide plate that includes a first main surface and a second main surface, and includes a first waveguide, a second waveguide, and a third waveguide, the second main surface being opposite to the first main surface, the third waveguide being optically coupled to the first waveguide and the second waveguide through a branch portion, and the first waveguide, the second waveguide, and the third waveguide being formed in parallel to the first main surface and the second main surface; an image pickup device including a light receiving surface and a rear surface, the rear surface being opposite to the light receiving surface and being disposed opposite to the first main surface of the optical waveguide plate; a first optical device and a second optical device mounted on the optical waveguide plate; one optical fiber disposed perpendicularly to the second main surface of the optical waveguide plate; a ferrule that includes a front surface and a rear surface, and includes a through hole into which the optical fiber is inserted and fixed, the rear surface being opposite to the front surface, the front surface being disposed opposite to the second main surface of the optical waveguide plate, and the through hole penetrating through the front surface to the rear surface; and a plurality of conductive wires respectively electrically connected to any one of the image pickup device, the first optical device, and the second optical device. The optical waveguide plate includes a reflection surface at an end part of the third waveguide, the first waveguide is optically coupled to the first optical device, the second waveguide is optically coupled to the second optical device, the third waveguide is optically coupled to the optical fiber through the reflection surface, the ferrule includes a notch on the front surface, distal end portions of the plurality of conductive wires are held between the second main surface of the optical waveguide plate and a surface of the notch of the ferrule, and the optical waveguide plate, the first optical device, the second optical device, the optical fiber, the ferrule, and the plurality of conductive wires are disposed within a plane of projection of the image pickup device as observed from an optical axis direction.

DETAILED DESCRIPTION OF THE PREFERRED EMBODIMENTS

First Embodiment

Figure 1:
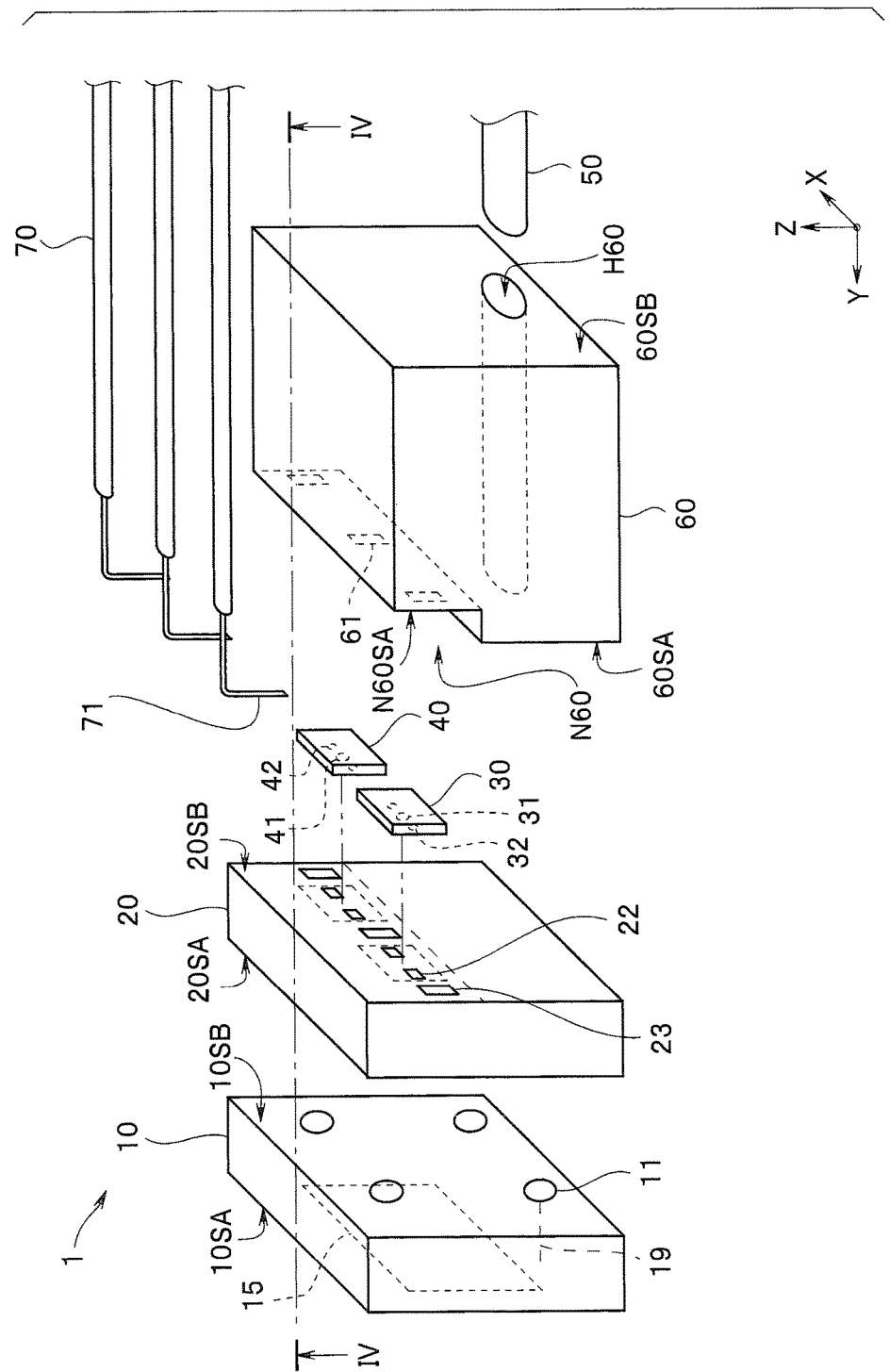
FIG. 1 is an exploded view of an image pickup module according to a first embodiment.

As illustrated in FIG. 1, an image pickup module 1 according to the present embodiment includes an image pickup device 10, an optical waveguide plate 20, a first optical device 30, a second optical device 40, one optical fiber 50, a ferrule 60, and a plurality of conductive wires 70. The image pickup device 10, the optical waveguide plate 20, and the ferrule 60 are stacked. The plurality of conductive wires 70 are respectively electrically connected to any one of the image pickup device 10, the first optical device 30 and the second optical device 40.

Note that, in the following description, a direction in which a value of Y axis in the drawing is increased is referred to as a front direction. In addition, it should be noted that the drawings based on respective embodiments are schematic diagrams, and relationship between a thickness and a width of each portion, thicknesses ratios and relative angles among the respective portions, and the like do not reflect actual things. Dimensional relationship and ratios may also differ from one drawing to another. In addition, illustration of a part of the components is omitted in some cases.

In the image pickup module 1, the first optical device 30 and the second optical device 40 are each a VCSEL (vertical cavity surface emitting LASER), that is, a light emitting device that emits an optical signal to a light emitting surface (XZ plane) in a perpendicular direction (Y-axis direction). The first optical device 30 and the second optical device 40 generate optical signals with different wavelengths. For example, a first optical signal L1 generated by the first optical device 30 includes a wavelength λ1 of 850 nm, and a second optical signal L2 generated by the second optical device 40 includes a wavelength X2 of 1300 nm.

For example, the first optical device 30 and the second optical device 40 each including excessively small dimensions of 250 μm×300 μm in a planar view respectively include light emitting portions 31 and 41 and connection terminals (bumps) 32 and 42 on light emitting surfaces. The light emitting portions 31 and 41 each include a diameter of 20 μm. The connection terminals 32 and 42 are respectively electrically connected to the light emitting portions 31 and 41.

A light receiving surface 10SA of the image pickup device 10 includes a light receiving portion 15 including a CCD image sensor or a CMOS image sensor, a peripheral circuit (not illustrated), and the like that are provided on a silicon substrate. The image pickup device 10 may be of a Back-Side-Illumination type. The image pickup device 10 converts light received by the light receiving surface 10SA into an image pickup signal, and outputs, for example, through a through wiring 19, the image pickup signal from external connection terminals 11 that are arranged on a rear surface 10SB opposite to the light receiving surface 10SA. The other external connection terminal is provided with an image pickup device driving signal.

Although not illustrated, the image pickup signal outputted from the image pickup device 10 is digitalized, and is further converted into an analog pulse signal as an optical device driving signal to cause the optical device (LASER) to emit light. The optical device driving signal is provided to the connection terminals 32 and 42 of the respective optical devices.

An unillustrated cover glass and an image pickup optical system are arranged on the light receiving surface 10SA of the image pickup device 10. The image pickup device 10 is fabricated by a wafer-level chip size package (WL-CSP) method. In other words, a glass wafer is bonded to a light receiving surface of a silicon wafer in which a plurality of light receiving portions and the like are formed by a well-known semiconductor forming technique, and a bonded wafer is accordingly fabricated. The bonded wafer is cut into a plurality of image pickup devices 10 after a through wiring is arranged on the bonded wafer from the silicon wafer side. The image pickup device 10 fabricated by the WL-CSP method has the dimension (XZ direction) same as the dimension of the cover glass in a planar view observed from an optical axis direction (Y-axis direction).

The optical waveguide plate 20 is a polymer optical waveguide plate including a first main surface 20SA and a second main surface 20SB opposite to the first main surface 20SA.

Figure 2:
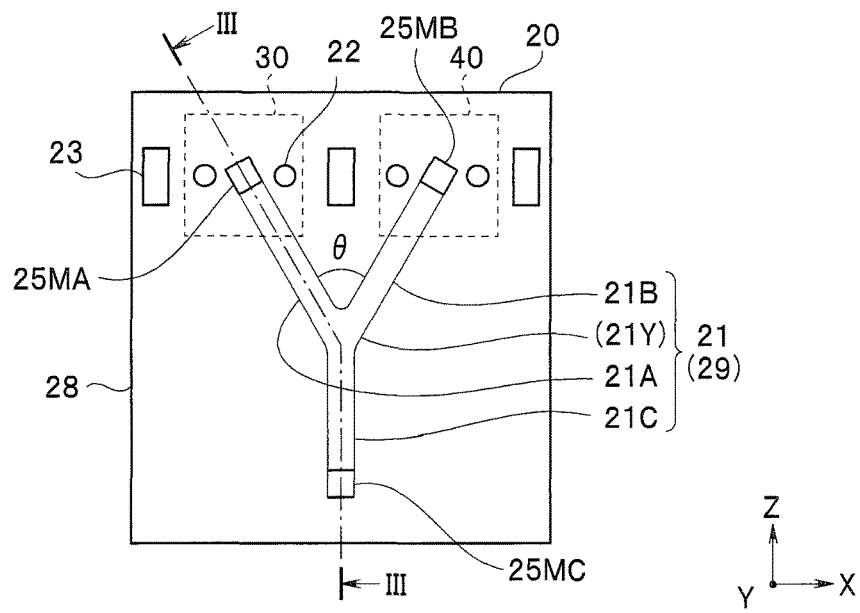
FIG. 2 is a rear view of an optical waveguide plate of the image pickup module according to the first embodiment.
Figure 3:
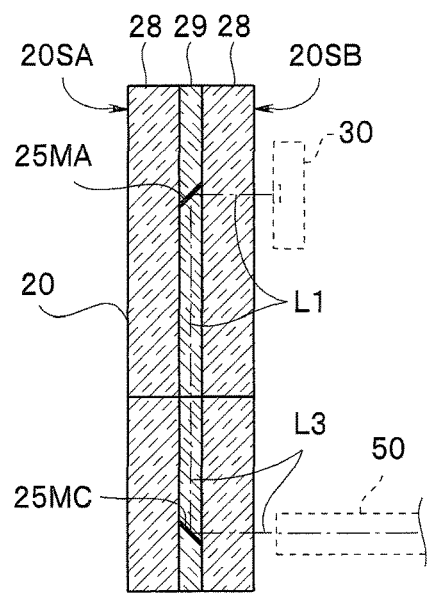
FIG. 3 is a cross-sectional view of the optical waveguide plate of the image pickup module according to the first embodiment taken along a line III-III in FIG. 2.

As illustrated in FIG. 2 and FIG. 3, the optical waveguide plate 20 includes, as main members, a core 29 and a cladding 28. The core 29 includes a first resin with a refractive index n1. The cladding 28 includes a second resin with a refractive index n2 and surrounds the core 29. The refractive index n1 is greater than the refractive index n2. To perform efficient optical transmission, a difference between the refractive index n1 of the core 29 and the refractive index n2 of the cladding 28 is preferably 0.05 or more and 0.20 or lower.

For example, the core 29 and the cladding 28 each include a fluorinated polyimide resin with a refractive index of 1.60 to 1.75, excellent in heat resistance, transparency, and isotropy.

As illustrated in FIG. 2, the core 29 configures the optical waveguide plate 20 that is formed in parallel to the first main surface 20SA and the second main surface 20SB. In other words, the core 29 configures a waveguide 21 that includes a first waveguide 21A, a second waveguide 21B, and a third waveguide 21C. The third waveguide 21C is optically coupled to the first waveguide 21A and the second waveguide 21B through a substantially Y-shaped branch portion 21Y. The branch portion 21Y may be regarded as a part of the first waveguide 21A, the second waveguide 21B, and the third waveguide 21C.

Note that a loss is small and transmission efficiency is high as a branch angle θ of the branch portion 21Y is smaller. The branch portion 21Y is preferably formed in a multistage or a curved substantially Y-shape in which the branch angle θ is gradually increased, rather than a Y-shaped branch portion in which three straight waveguides intersect.

The optical waveguide plate 20 includes a first reflection surface 25MA with a reflection angle of 90 degrees at an end part of the first waveguide 21A, a second reflection surface 25MB with a reflection angle of 90 degrees at an end part of the second waveguide 21B, and a reflection surface (third reflection surface) 25MC with a reflection angle of 90 degrees at an end part of the third waveguide 21C. Note that the reflection surface with the reflection angle of 90 degrees is an inclined surface inclined by 45 degrees with respect to the second main surface 20SB.

Each of the reflection surfaces is formed by, for example, polishing processing or grinding processing using a diamond blade of the end part of the corresponding waveguide. A reflection film containing a metal such as aluminum may be arranged on each of the reflection surfaces in order to increase reflectance.

An optical path orthogonal to the first main surface 20SA of the optical waveguide plate 20 and an optical path (waveguide) parallel to the first main surface 20SA are optically coupled to each other by the reflection surfaces with the reflection angle of 90 degrees.

In other words, the first optical signal L1 generated by the first optical device 30 that is arranged right above the first reflection surface 25MA is guided in the first waveguide 21A through the first reflection surface 25MA. Likewise, the second optical signal L2 generated by the second optical device 40 that is arranged right above the second reflection surface 25MB is guided in the second waveguide 21B through the second reflection surface 25MB.

For example, the reflection angle of the first reflection surface 25MA is not limited to 90 degrees as long as the first optical signal L1 generated by the first optical device 30 is efficiently guided in the first waveguide 21A. In other words, it is sufficient to configure each of the reflection surfaces so as to optically couple the optical devices and the optical fiber to the corresponding waveguide.

Further, the first optical signal L1 and the second optical signal L2 are multiplexed at the branch portion 21Y and a multiplexed third optical signal L3 is guided in the third waveguide 21C. Thereafter, the third optical signal L3 enters the optical fiber 50 through the third reflection surface 25MC.

Note that, as described later, not only an optical circuit that includes the waveguide 21 and the like but also a wiring including a conductor are arranged on the optical waveguide plate 20. The optical waveguide plate 20 includes the plurality of conductive wires 70 that are each electrically connected to any one of the image pickup device 10 and the first optical device 30 and the second optical device 40. In other words, the optical waveguide plate 20 includes a function of a wiring board that electrically connects the image pickup device 10, the first optical device 30, the second optical device 40, and the conductive wires 70.

The optical fiber 50 is disposed such that the optical axis direction is perpendicular to the second main surface 20SB of the optical waveguide plate 20. The optical fiber 50 includes, for example, an outer diameter (cladding diameter) of 125 μm, and a core diameter of 50 μm. Note that, to cause the third optical signal L3 guided by the optical waveguide plate 20 to efficiently enter a core, a cross-sectional area of the waveguide and an area of each of the reflection surfaces of the optical waveguide plate 20 are preferably slightly smaller than a cross-sectional area of the core of the optical fiber 50.

Figure 4:
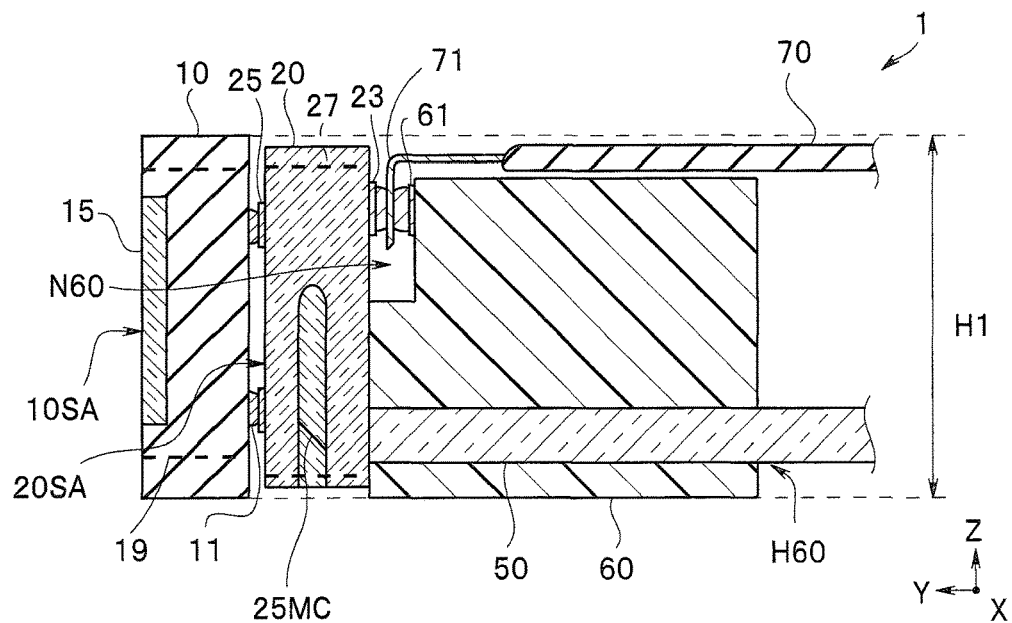
FIG. 4 is a cross-sectional view of the image pickup module according to the first embodiment.
Figure 5:
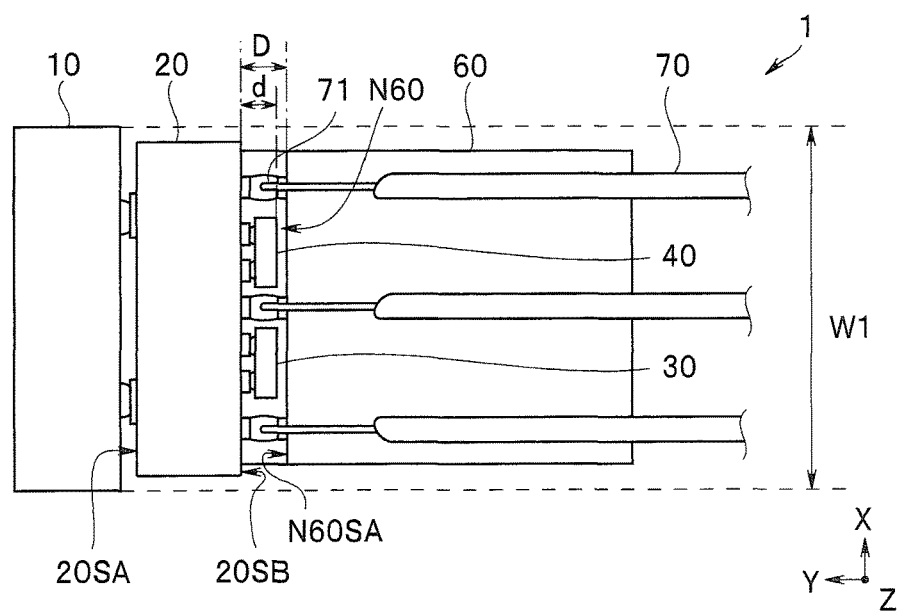
FIG. 5 is a top view of the image pickup module according to the first embodiment.

As illustrated in FIG. 1, FIG. 4, and FIG. 5, the ferrule 60 includes a through hole H60 that penetrates from a front surface 60SA to a rear surface 60SB. The optical fiber 50 is inserted into and fixed to the through hole H60. The through hole H60 includes an inner diameter slightly larger than the outer diameter of the optical fiber 50. Note that FIG. 4 is a cross-sectional view taken along a line IV-IV in FIG. 1.

The ferrule 60 includes the front surface 60SA and the rear surface 60SB opposite to the front surface 60SA. The front surface 60SA is disposed opposite to and is stacked on the second main surface 20SB of the optical waveguide plate 20, and is bonded to the second main surface 20SB with an adhesive (not illustrated). Note that, to prevent the adhesive from entering the through hole H60 when the ferrule 60 is bonded to the optical waveguide plate 20, for example, an annular concave part or an annular convex part is preferably formed on the front surface 60SA along an opening of the through hole H60.

Further, the front surface 60SA of the ferrule 60 includes a notch N60. The notch N60 is a concave part that is the front surface 60SA partially cut. A front surface of the notch N60 is referred to as a notch surface N60SA. The notch surface N60SA is in parallel to the front surface 60SA of the ferrule 60.

To form the notch N60, a subtractive method in which a part of the front surface 60SA is cut to form the notch N60 through machining processing, or an additive method in which a surface other than the notch N60 is raised to relatively form the notch N60 may be used. In the additive method, for example, another member may be bonded to the front surface 60SA to raise the surface. Further, the ferrule 60 including the notch N60 may be fabricated by integral molding.

In the image pickup module 1, the first optical device 30 and the second optical device 40 are housed in the notch N60. In other words, a depth (dimension in Y direction) D of the notch N60 is equal to or greater than a thickness (dimension in Y direction) d of each of the first optical device 30 and the second optical device 40 (more strictly, total length of thickness d and height of bonding part).

Moreover, in the image pickup module 1, distal end portions 71 of the respective conductive wires 70 are inserted into and fixed to the notch N60. In other words, the distal end portions 71 are held between the second main surface 20SB of the optical waveguide plate 20 and the notch surface N60SA of the ferrule 60. Note that a space between the second main surface 20SB of the optical waveguide plate 20 and the notch surface N60SA of the ferrule 60 is sealed with a sealing resin (not illustrated).

As described above, the optical waveguide plate 20 of the image pickup module 1 is the wiring board on which not only the optical circuit but also the electric circuit including the conductor are arranged.

As illustrated in FIG. 4 and FIG. 5, a plurality of electrodes 25 that are respectively bonded to the external connection terminals 11 of the image pickup device 10 are arranged on the first main surface 20SA of the optical waveguide plate 20. A space between the optical waveguide plate 20 and the image pickup device 10 is preferably sealed with a sealing resin (not illustrated).

Further, the optical waveguide plate 20 includes, for example, through wirings 27 that respectively connect the electrodes 25 of the first main surface 20SA and electrodes 23 of the second main surface. Moreover, a plurality of electrodes 22 that are each connected to the connection terminal 32 of the first optical device 30 or the connection terminal 42 of the second optical device 40 are arranged on the second main surface 20SB of the optical waveguide plate 20. Furthermore, a plurality of wiring patterns (not illustrated) that include, for example, wirings connecting the electrodes 23 and the electrodes 22 are arranged on the second main surface 20SB.

On other hand, electric wirings are also arranged on the ferrule 60 holding the optical fiber 50. In other words, electrodes 61 to which the conductive wires 70 are bonded, etc. are arranged on the notch surface N60SA. The ferrule 60 includes ceramics or a molded interconnect device (MID). In particular, the ferrule 60 including the MID has high flexibility in wiring design. Therefore, an electronic component such as a chip capacitor is easily mounted on the ferrule 60.

The distal end portions 71 of the respective plurality of conductive wires 70 are bonded to the electrodes 23 on the second main surface 20SB of the optical waveguide plate 20 and the electrodes 61 on the notch surface N60SA of the ferrule 60 through soldering.

Note that the distal end portions 71 of the respective conductive wires 70 may be bonded only to the electrodes 23 on the second main surface 20SB of the optical waveguide plate 20, and a space with the notch surface N60SA of the ferrule 60 at the bonding part may be sealed with a sealing resin.

The distal end portions 71 of the respective conductive wires 70 have high bonding strength because the distal end portions 71 are held between the optical waveguide plate 20 and the ferrule 60. Therefore, for example, even if stress is applied to the conductive wires 70 when the image pickup module 1 is assembled to other member, the conductive wires 70 are not detached, and reliability of the conductive wires 70 is not deteriorated due to contact failure.

If the notch N60 of the ferrule 60 can house the other electronic component, the other electronic component may be mounted on the second main surface 20SB of the optical waveguide plate 20 in addition to the first optical device 30 and the second optical device 40. Examples of the other electronic component include a driving IC for each of the first optical device 30 and the second optical device 40, a chip capacitor, and a chip inductor.

In addition, as illustrated in FIG. 4 and FIG. 5, in the image pickup module 1, the components other than the image pickup device 10 (optical waveguide plate 20, first optical device 30, second optical device 40, optical fiber 50, ferrule 60, and conductive wires 70) are disposed within a plane of projection of the image pickup device 10 as observed from the optical axis direction (Y direction). In other words, the dimension of each of the optical waveguide plate 20 and the ferrule 60 in a planar view (XZ dimension) observed from the optical axis direction (Y direction) is equal to or smaller than the dimension of the image pickup device 10 in the planar view. Further, the first optical device 30 and the second optical device 40 are disposed on the second main surface 20SB of the optical waveguide plate 20. Moreover, the conductive wires 70 are disposed on the ferrule 60 that has a height (dimension in Z direction) less than the height of the optical waveguide plate 20.

As described above, in the image pickup module 1, the first optical device 30 and the second optical device 40 are housed in the notch N60 of the ferrule 60. Further, since the optical waveguide plate 20 includes the waveguide that is extended and disposed in the in-plane direction orthogonal to the length direction and include a light branching function, the image pickup module 1 is small in size with small length (dimension in Y direction).

In addition, a height H1 (dimension in Z-axis direction) of the image pickup module 1 corresponds to the height of the image pickup device 10, and a width W1 (dimension in X-axis direction) of the image pickup module 1 corresponds to the width of the image pickup device 10. Therefore, the image pickup module 1 has a small diameter.

In other words, the image pickup module 1 is small in diameter and size, and has high bonding reliability of the conductive wires 70.

Note that, in the image pickup module 1, the first optical device 30 and the second optical device 40 are each the light emitting device. The first optical device 30 and the second optical device 40, however, may be a light receiving device including a light receiving portion, such as a photodiode (PD). The photodiode converts an optical signal that has entered a light receiving surface from a perpendicular direction (Y-axis direction) into an electric signal, and outputs the electric signal. For example, an ultra-small light receiving device that has a dimension of 350 µm×300 µm in a planar view includes, on the light receiving surface, the light receiving portion having a diameter of 50 µm and a connection terminal that is electrically connected to the light receiving portion and outputs the electric signal.

In addition, as described later, the first optical device may be a light emitting device and the second optical device may be a light receiving device. Alternatively, the first optical device may be a light receiving device and the second optical device may be a light emitting device.

Modifications of First Embodiment

Next, image pickup modules 1A and 1B according to modifications of the first embodiment are described. The image pickup modules 1A and 1B are each similar to the image pickup module 1 and have the same effects as the effects of the image pickup module 1. Therefore, components having the same function are denoted by the same reference numeral, and description of the components is omitted.

Modification 1 of First Embodiment

Figure 6:
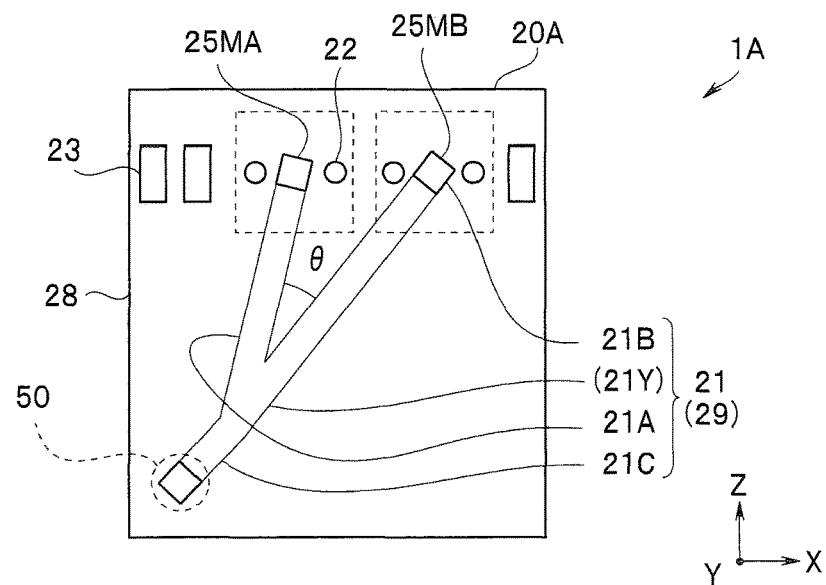
FIG. 6 is a rear view of an optical waveguide plate of an image pickup module according to a modification 1 of the first embodiment.

As illustrated in FIG. 6, in the image pickup module 1A according to a modification 1, the optical fiber 50 is disposed at a corner part of the second main surface 20SB of an optical waveguide plate 20A including a rectangular shape in a planar view. In other words, an end part of the third waveguide 21C of the optical waveguide plate 20A is disposed at the corner part of the second main surface 20SB. Further, the third waveguide 21C is extended and disposed along a diagonal direction of the optical waveguide plate 20A.

As described above, the loss is small as the branch angle θ of the Y-shaped branch portion 21Y is smaller. Therefore, the length of the waveguide is preferably large. In the image pickup module 1A, the loss of the Y-shaped branch portion 21Y is small because the waveguide is extended and disposed along the diagonal direction of the optical waveguide plate 20A.

Modification 2 of First Embodiment

Figure 7:
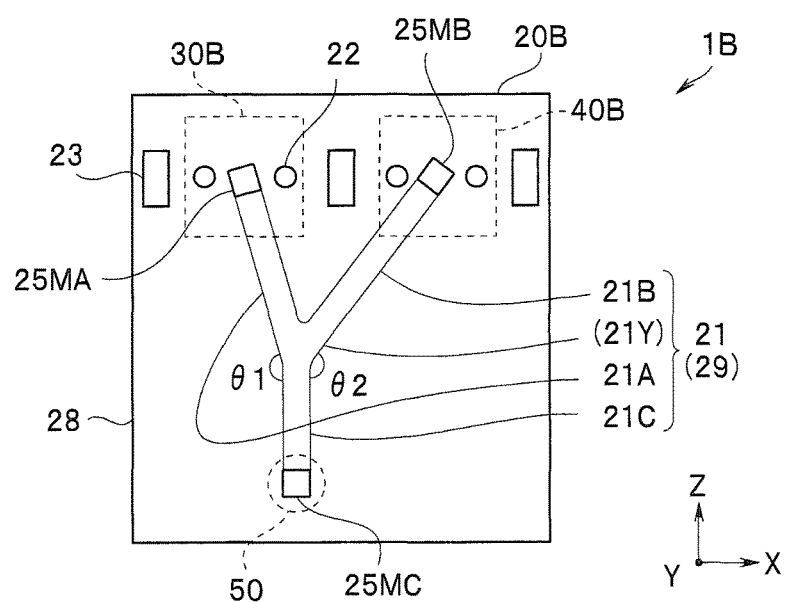
FIG. 7 is a rear view of an optical waveguide plate of an image pickup module according to a modification 2 of the first embodiment.

As illustrated in FIG. 7, in the image pickup module 1B according to a modification 2, a first optical device 30B is a light receiving device, and a second optical device 40B is a light emitting device. In other words, the image pickup module 1B configures a bidirectional communication optical circuit, and the optical fiber 50 guides the first optical signal L1 and the second optical signal L2 in opposite directions at the same time.

The first waveguide 21A guides the first optical signal (optical control signal) guided by the optical fiber 50, to the first optical device 30B as the light receiving device. A control signal that has been O/E converted from the first optical signal and outputted by the first optical device 30B is provided to the image pickup device 10 through a TIA (transimpedance amplifier) and an LA (limiting amplifier). The TIA, the LA and the like each including a semiconductor device are housed in, for example, the notch N60 of the ferrule 60. On the other hand, the second waveguide 21B guides, to the optical fiber 50, the second optical signal (optical image pickup signal) that has been E/O converted from the image pickup signal by the second optical device 40B as the light emitting device and generated.

Note that the first waveguide 21A preferably has a length less than a length of the second waveguide 21B. This is because a quantity of light received by the light receiving device is typically lower than a quantity of light generated by the light emitting device, and therefore, the light is preferably more effectively transmitted.

Furthermore, a branch angle θ1 between the first waveguide 21A and the third waveguide 21C is preferably greater than a branch angle θ2 between the second waveguide 21B and the third waveguide 21C and is closer to 180 degrees because of a small loss.

Second Embodiment

Next, an image pickup module 1C according to a second embodiment is described. The image pickup module 1C is similar to the image pickup module 1 and has the effects same as the effects of the image pickup module 1. Therefore, components having the same function are denoted by the same reference numeral, and description of the components is omitted.

Figure 8:
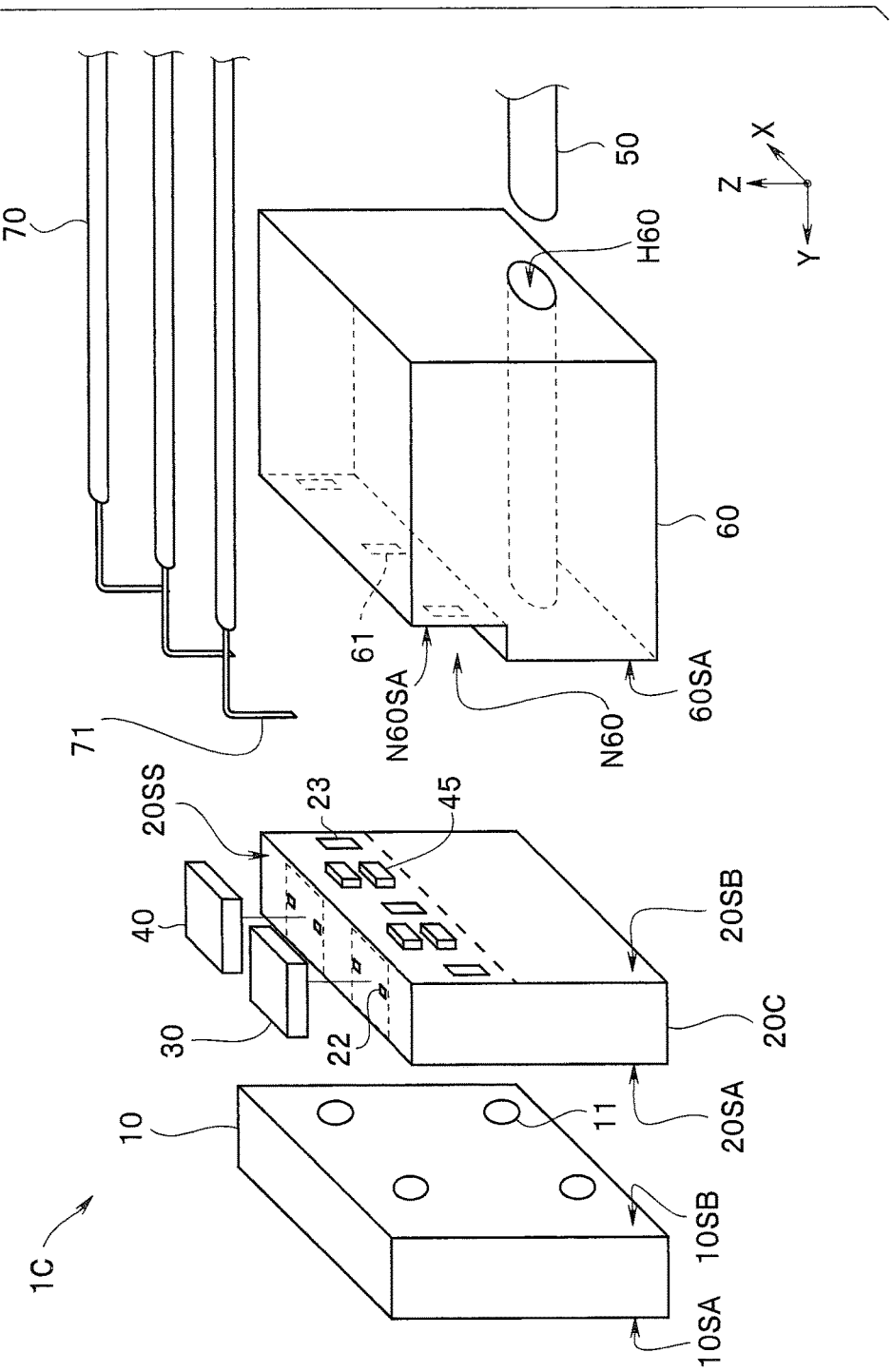
FIG. 8 is an exploded view of an image pickup module according to a second embodiment.

As illustrated in FIG. 8, in the image pickup module 1C, the first optical device 30 and the second optical device 40 are mounted on a side surface 20SS of an optical waveguide plate 20C. The side surface 20SS of the rectangular parallelepiped optical waveguide plate 20C is orthogonal to the first main surface 20SA and the second main surface 20SB.

In other words, the electrodes 22 are arranged on the side surface 20SS of the optical waveguide plate 20C. Further, a length of the side surface 20SS (dimension in optical axis direction: dimension in Y-axis direction) is greater than the length of each of the first optical device 30 and the second optical device 40.

Further, although not illustrated, the first waveguide 21A and the second waveguide 21B are extended up and disposed to the side surface 20SS. A reflection surface is not formed on the end part of the first waveguide 21A and the end part of the second waveguide 21B as a matter of course.

The image pickup module 1C is easily manufactured because it is unnecessary to form a reflection surface at the end part of the first waveguide 21A and the end part of the second waveguide 21B. In addition, another electronic component 45 (e.g., TIA or LA) is easily housed in the notch of the ferrule 60.

Note that the image pickup module 1C includes the configuration same as the configuration of the image pickup module 1A or 1B to achieve the effects same as the effects of the image pickup module 1A or 1B as a matter of course.

Third Embodiment

Figure 9:
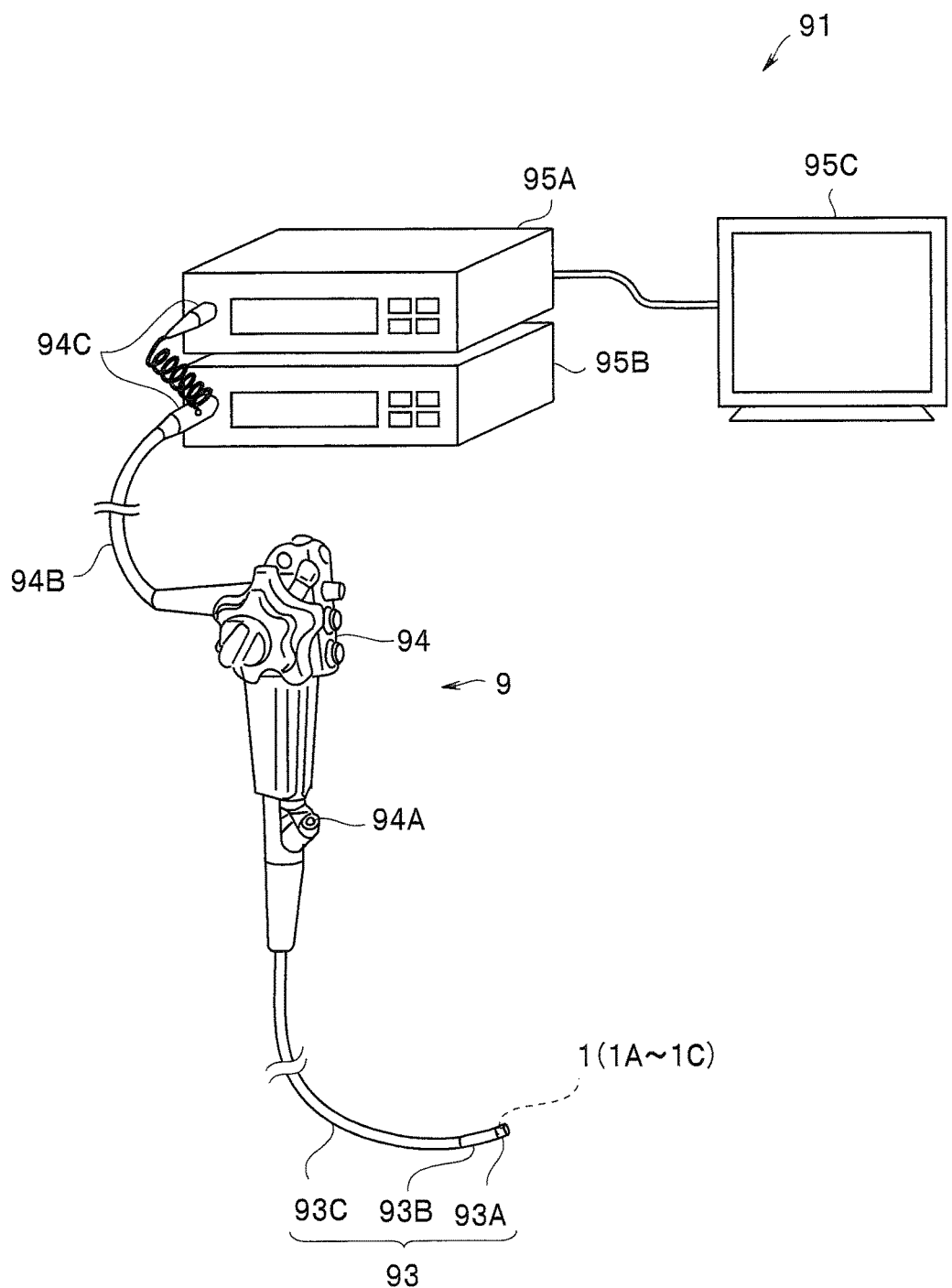
FIG. 9 is a perspective view of an endoscope system including an endoscope according to a third embodiment.

As illustrated in FIG. 9, an endoscope 9 according to the present embodiment includes any of the image pickup modules 1 to 1C at a rigid distal end portion 93A of the insertion section 93.

An endoscope system 91 includes the endoscope 9, a processor 95A, a light source apparatus 95B, and a monitor 95C. The endoscope 9 picks up an image inside a body of a subject through insertion of the insertion section 93 into a body cavity of the subject.

An operation section 94 that includes various kinds of buttons for operation of the endoscope 9 is arranged on proximal end side of the insertion section 93 of the endoscope 9. The operation section 94 includes a treatment instrument insertion opening 94A that is a channel to insert treatment instruments such as biological forceps, an electric scalpel, and an inspection probe into the body cavity of the subject.

The insertion section 93 includes the rigid distal end portion 93A in which any of the image pickup modules 1 to 1C is arranged, a bending portion 93B configured to be bendable continuously provided on proximal end side of the rigid distal end portion 93A, and a flexible tube portion 93C continuously provided on proximal end side of the bending portion 93B. The bending portion 93B is bent by operation of the operation section 94.

A universal cord 94B is connected to the processor 95A and the light source apparatus 95B through a connector 94C. The processor 95A controls the entire endoscope system 91, and performs signal processing on the image pickup signal outputted from any of the image pickup modules 1 to 1C and outputs a resultant signal as an image signal. The monitor 95C displays the image signal outputted from the processor 95A.

For example, in the endoscope 9 in which the image pickup module 1 including two light emitting devices is disposed at the rigid distal end portion 93A, the image pickup signal outputted from the image pickup device 10 is divided into a first image pickup signal and a second image pickup signal. Further, a first optical image pickup signal and a second optical image pickup signal that have been respectively E/O converted by the optical devices are multiplexed, and the multiplexed signal is transmitted to the operation section 94 through one optical fiber 50 passing through the insertion section 93.

Although not illustrated, for example, an optical transmission module that includes a demultiplexer and two light receiving devices is disposed in the operation section 94. The demultiplexer separates the first optical image pickup signal and the second optical image pickup signal. The two light receiving devices respectively perform O/E conversion of the demultiplexed optical signals. The image pickup signal that has been converted into electric signals and merged in the optical transmission module of the operation section 94 is transmitted to the processor 95A through a conductive wire passing through the universal cord 94B.

Note that the optical fiber may pass through the universal cord 94B, and the O/E conversion may be performed by an optical transmission module that is disposed in the connector 94C or the processor 95A.

In the endoscope 9, the insertion section 93 has a small diameter because the signal is transmitted through the optical fiber. In addition, each of the image pickup modules 1 to 1C is small in diameter and size. Therefore, the rigid distal end portion 93A of endoscope 9 has low invasiveness due to being small in diameter and size.

Note that the endoscope of the present embodiment is not limited to a flexible endoscope including the flexible tube portion 93C, and may be a rigid endoscope or a capsule endoscope.

The present invention is not limited to the above-described embodiments, the above-described modifications, and the like, and various modifications, combinations, and applications of the present invention may be made without departing from the scope of the present invention.

What is claimed is:

1. An image pickup module, comprising:
   a polymer optical waveguide plate that includes a first main surface and a second main surface, and includes a first waveguide, a second waveguide, and a third waveguide, the second main surface being opposite to the first main surface, the third waveguide being optically coupled to the first waveguide and the second waveguide through a branch portion, and the first waveguide, the second waveguide, and the third waveguide being formed in parallel to the first main surface and the second main surface;
   an image pickup device including a light receiving surface and a rear surface, the rear surface being opposite to the light receiving surface and being disposed opposite to the first main surface of the optical waveguide plate;
   a first optical device and a second optical device mounted on the optical waveguide plate;
   one optical fiber disposed perpendicularly to the second main surface of the optical waveguide plate;
   a ferrule that includes a front surface and a rear surface, and includes a through hole into which the optical fiber is inserted and fixed, the rear surface being opposite to the front surface, the front surface being disposed opposite to the second main surface of the optical waveguide plate, and the through hole penetrating through the front surface to the rear surface; and
   a plurality of conductive wires respectively electrically connected to any one of the image pickup device, the first optical device, and the second optical device, wherein
   the optical waveguide plate includes a reflection surface at an end part of the third waveguide,
   the first waveguide is optically coupled to the first optical device, the second waveguide is optically coupled to the second optical device, and the third waveguide is optically coupled to the optical fiber through the reflection surface,
   the ferrule includes a notch on the front surface,
   distal end portions of the plurality of conductive wires are held between the second main surface of the optical waveguide plate and a surface of the notch of the ferrule, and
   the optical waveguide plate, the first optical device, the second optical device, the optical fiber, the ferrule, and the plurality of conductive wires are disposed within a plane of projection of the image pickup device as observed from an optical axis direction.

2. The image pickup module according to claim 1, wherein
   the optical waveguide plate includes a first reflection surface at an end part of the first waveguide and a second reflection surface at an end part of the second waveguide,
   the first optical device and the second optical device are mounted on the second main surface of the optical waveguide plate, and
   the first optical device and the second optical device are housed in the notch on the front surface of the ferrule.

3. The image pickup module according to claim 1, wherein the first optical device and the second optical device are mounted on a side surface of the optical waveguide plate.

4. The image pickup module according to claim 1, wherein the optical fiber is disposed at a corner part of the second main surface of the optical waveguide plate including a rectangular shape in a planar view, and the third waveguide is extended and disposed along a diagonal direction of the optical waveguide plate.

5. The image pickup module according to claim 1, wherein each of the first optical device and the second optical device is a light emitting device or a light receiving device.

6. The image pickup module according to claim 1, wherein the first optical device is a light emitting device and the second optical device is a light receiving device.

7. The image pickup module according to claim 6, wherein a length of the second waveguide is less than a length of the first waveguide.

8. An endoscope comprising the image pickup module according to claim 1 at a rigid distal end portion of an insertion section.

* * * * *